(12) United States Patent
Wang et al.

(10) Patent No.: US 9,101,698 B2
(45) Date of Patent: Aug. 11, 2015

(54) BIOABSORBABLE STENT WITH RADIOPAQUE LAYER AND METHOD OF FABRICATION

(75) Inventors: Yunbing Wang, Sunnyvale, CA (US); David C. Gale, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1274 days.

(21) Appl. No.: 11/951,232

(22) Filed: Dec. 5, 2007

(65) Prior Publication Data
US 2009/0149940 A1   Jun. 11, 2009

(51) Int. Cl.
*A61L 31/18* (2006.01)
*A61L 31/12* (2006.01)
*A61L 31/14* (2006.01)

(52) U.S. Cl.
CPC ............. *A61L 31/18* (2013.01); *A61L 31/12* (2013.01); *A61L 31/148* (2013.01)

(58) Field of Classification Search
CPC ....................................................... A61L 31/18
USPC ........................................ 623/1.34; 264/150
See application file for complete search history.

(56) References Cited

U.S. PATENT DOCUMENTS

| | | | |
|---|---|---|---|
| 6,200,338 B1 * | 3/2001 | Solomon et al. ............. | 623/1.34 |
| 6,585,755 B2 | 7/2003 | Jackson et al. | |
| 6,730,120 B2 | 5/2004 | Berg et al. | |
| 6,926,733 B2 | 8/2005 | Stinson | |
| 2003/0104028 A1 | 6/2003 | Hossainy | |
| 2003/0199993 A1 * | 10/2003 | Gellman et al. ........... | 623/23.75 |
| 2005/0064224 A1 | 3/2005 | Bavaro et al. | |
| 2005/0209680 A1 | 9/2005 | Gale et al. | |
| 2006/0271170 A1 * | 11/2006 | Gale et al. .................... | 623/1.49 |
| 2007/0038292 A1 | 2/2007 | Danielpour | |
| 2008/0009939 A1 | 1/2008 | Gueriguian et al. | |
| 2008/0015684 A1 | 1/2008 | Wu | |
| 2008/0058919 A1 | 3/2008 | Kramer-Brown et al. | |
| 2008/0086199 A1 * | 4/2008 | Dave et al. ................... | 623/1.42 |
| 2008/0269874 A1 * | 10/2008 | Wang et al. .................. | 623/1.34 |

FOREIGN PATENT DOCUMENTS

| | | |
|---|---|---|
| EP | 0 894 503 | 2/1999 |
| WO | WO 2004/023985 | 3/2004 |

OTHER PUBLICATIONS

Weill et al., ""Corrosion" of Tungsten Spirals. A disturbing Finding", Interventional Neuroradiology 4 pp. 337-340 (1998).
International Search Report for PCT/US2008/013370, mailed May 4, 2010, 7 pgs.
U.S. Appl. No. 11/818,304, filed Jan. 13, 2007, Gale et al.
U.S. Appl. No. 11/799,354, filed Apr. 30, 2007, Wang et al.
U.S. Appl. No. 11/968,600, filed Jan. 2, 2008, Wang.
Barrett et al. "Endovascular Embolization of Varicoceles: Resorption of Tungsten Coils in the Spermatic Vein", Cardiovasc. Intervent. Radiol. 23, pp. 457-459 (2000).
Butler et al., "In vivo degradation of tungsten embolisation coils", The British J. of Radiology 73, pp. 601-603 (2000).

(Continued)

*Primary Examiner* — Larry Thrower
(74) *Attorney, Agent, or Firm* — Squire Patton Boggs (US) LLP (57) ABSTRACT

Embodiments of a stent and methods of fabricating the same with a bioabsorbable radiopaque layer are disclosed.

11 Claims, 6 Drawing Sheets

(56) References Cited

OTHER PUBLICATIONS

Peuster et al., "Degradation of tungsten coils implanted into the subclavian artery of New Zealand white rabbits is not associated with local or systemic toxicity", Biomaterials 24 pp. 393-399 (2003).

Wei Li "Dissolution of tungsten coils leads to device failure after transcatheter embolisation of pathologic vessels", Heart 85, pp. 703-704 (2001).

* cited by examiner

FIG. 9B

BIOABSORBABLE STENT WITH RADIOPAQUE LAYER AND METHOD OF FABRICATION

BACKGROUND OF THE INVENTION

1. Field of the Invention

This invention relates to implantable medical devices, such as stents. In particular, the invention relates to bioabsorbable polymeric stents with a radiopaque layer.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The structure of stents is typically composed of scaffolding that includes a pattern or network of interconnecting structural elements or struts. The scaffolding can be formed from wires, tubes, or sheets of material rolled into a cylindrical shape. In addition, a medicated stent may be fabricated by coating the surface of either a metallic or polymeric scaffolding with a polymeric carrier. The polymeric scaffolding may also serve as a carrier of an active agent or drug.

The first step in treatment of a diseased site with a stent is locating a region that may require treatment such as a suspected lesion in a vessel, typically by obtaining an x-ray image of the vessel. To obtain an image, a contrast agent, which contains a radiopaque substance such as iodine is injected into a vessel. "Radiopacity" refers to the ability of a substance to absorb x-rays. The x-ray image depicts the lumen of the vessel from which a physician can identify a potential treatment region. The treatment then involves both delivery and deployment of the stent. "Delivery" refers to introducing and transporting the stent through a bodily lumen to a region in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen. In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn allowing the stent to self-expand.

The stent must be able to simultaneously satisfy a number of mechanical requirements. A stent must be capable of maintaining a desired degree of patency of a vessel. To accomplish this, the stent must be capable of withstanding the structural loads, namely radial compressive forces, imposed on the stent as it supports the walls of a vessel lumen. In addition to having adequate radial strength or hoop strength, the stent should be longitudinally flexible to allow it to be maneuvered through a tortuous vascular path and to enable it to conform to a deployment site that may not be linear or may be subject to flexure. The material from which the stent is constructed must allow the stent to undergo expansion, which typically requires substantial deformation of localized portions of the stent's structure. Once expanded, the stent must maintain its size and shape throughout its service life despite the various forces that may come to bear thereon, including the cyclic loading induced by the beating heart. Finally, the stent must be biocompatible so as not to trigger any adverse vascular responses.

In addition to meeting the mechanical requirements described above, it is desirable for a stent to be sufficiently radiopaque to be fluoroscopically visible under x-rays. Accurate stent placement is facilitated by real time visualization of the delivery of a stent. A cardiologist or interventional radiologist can track the delivery catheter through the patient's vasculature and precisely place the stent at the site of a lesion. This is typically accomplished by fluoroscopy or similar x-ray visualization procedures. For a stent to be fluoroscopically visible it must be more absorptive of x-rays than the surrounding tissue. Radiopaque materials in a stent may allow for its direct visualization.

It may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from bioerodable materials such as biodegradable polymers can be configured to completely erode only after the clinical need for them has ended.

However, all commercially available bioabsorbable polymers are radiolucent and do not possess sufficient radiographic density to be easily imaged by fluoroscopy. Biodegradable polymers tend to have x-ray absorption properties similar to body tissue.

SUMMARY OF THE INVENTION

Various embodiments of the present invention include a bioabsorbable stent comprising a stent scaffolding including a radiopaque layer and a support layer, the radiopaque layer comprising radiopaque material mixed within a first bioabsorbable polymer, the support layer formed from a second bioabsorbable polymer.

Further embodiments of the present invention include a method of fabricating a stent comprising: co-extruding a tube including a radiopaque layer and a support layer, the radiopaque layer comprising a radiopaque material mixed within a first bioabsorbable polymer, the support layer formed from a second bioabsorbable polymer; and cutting a stent pattern in the tube to form a stent comprising a scaffolding, the stent scaffolding including a support layer and a radiopaque layer, the scaffolding support layer formed from the tube support layer and the scaffolding radiopaque layer formed from the tube radiopaque layer Additional embodiments of the present invention include a method of fabricating a stent comprising: forming a radiopaque coating layer over at least a portion of a surface of a tube, the radiopaque coating layer comprising a radiopaque material mixed within a first bioabsorbable polymer, the tube formed from a second bioabsorbable polymer; and cutting a stent pattern in the coated tube to form a stent comprising a scaffolding, the stent scaffolding including a support layer and a radiopaque layer, the scaffolding support layer formed from the tube formed from the first bioabsorbable polymer and the scaffolding radiopaque layer formed from the radiopaque coating layer.

DETAILED DESCRIPTION OF THE INVENTION

Embodiments of the present invention may be applied to stents and, more generally, to implantable medical devices such as, but not limited to, self-expandable stents, balloon-expandable stents, stent-grafts, vascular grafts, or generally, tubular implantable medical devices.

A stent can have virtually any structural pattern that is compatible with a bodily lumen in which it is implanted. Typically, a stent is composed of a pattern or network of circumferential and longitudinally extending interconnecting structural elements or struts. In general, the struts are arranged in patterns, which are designed to contact the lumen walls of a vessel and to maintain vascular patency. A myriad of strut patterns are known in the art for achieving particular design goals. A few of the more important design characteristics of stents are radial or hoop strength, expansion ratio or coverage area, and longitudinal flexibility. The present invention is applicable to virtually any stent design and is, therefore, not limited to any particular stent design or pattern. One embodiment of a stent pattern may include cylindrical rings composed of struts. The cylindrical rings may be connected by linking or connecting struts.

In some embodiments, a stent of the present invention may be formed from a tube by laser cutting the pattern of struts in the tube. The stent may also be formed by laser cutting a polymeric sheet, rolling the pattern into the shape of the cylindrical stent, and providing a longitudinal weld to form the stent. Other methods of forming stents are well known and include chemically etching a polymeric sheet and rolling and then welding it to form the stent.

Figure 1:
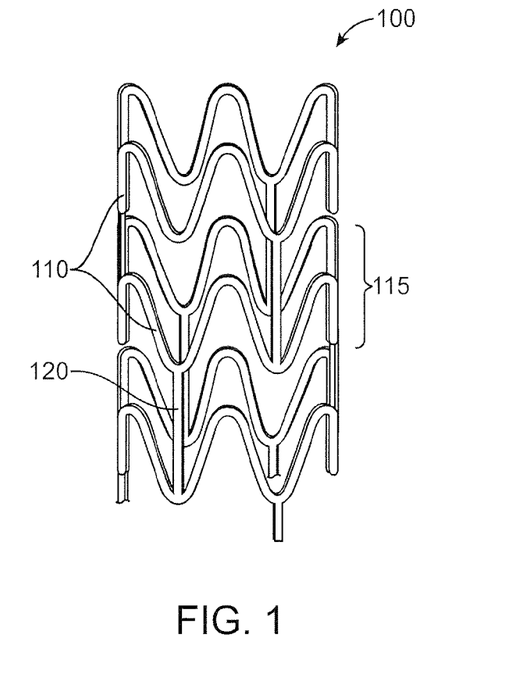
FIG. 1 depicts an exemplary stent.

FIG. 1 depicts an exemplary stent 100 with struts 110 that form cylindrical rings 115 which are connected by linking struts 120. The cross-section of the struts in stent 100 is rectangular-shaped. The cross-section of struts is not limited to what has been illustrated, and therefore, other cross-sectional shapes are applicable with embodiments of the present invention. The pattern should not be limited to what has been illustrated as other stent patterns are easily applicable with embodiments of the present invention.

A stent can be made of a biostable polymer, bioabsorbable polymer, or both. In general, polymers can be biostable, bioabsorbable, biodegradable, bioerodable, dissolvable, or water soluble. Biostable refers to polymers that are not bioabsorbable. The terms biodegradable, bioabsorbable, and bioerodable, biosoluble, as well as degraded, eroded, absorbed, and dissolved refer to polymers that are capable of being completely eroded or absorbed when exposed to bodily fluids such as blood and can be gradually resorbed, absorbed and/or eliminated by the body.

Some bioabsorbable polymers absorb due to chemical degradation that occurs in a polymer upon exposure to bodily fluids as in a vascular environment. Chemical degradation refers to degradation of a polymer due to chemical reaction of the polymer with bodily fluids or substances within bodily fluids. The chemical degradation can result in a decrease in molecular weight, deterioration of mechanical properties, and decrease in mass due to erosion. Mechanical properties may correspond to strength and modulus of the polymer. Deterioration of the mechanical properties of the polymer decreases the ability of a stent, for example, to provide mechanical support in a vessel. The chemical degradation can be the result of hydrolysis, oxidation, enzymolysis, and/or metabolic processes. Additionally, some bioabsorbable polymers are water soluble. A water soluble polymer corresponds to a polymer that is capable of dissolving in water in addition to, or even in the absence of chemical degradation of the polymer.

As indicated above, a stent made from a bioabsorbable polymer is intended to remain in the body for a duration of time until its intended function of, for example, maintaining vascular patency and/or drug delivery is accomplished. After the process of degradation, erosion, absorption, dissolution, and/or resorption has been completed, no portion of the bioabsorbable stent, or a bioabsorbable portion of the stent will remain. In some embodiments, very negligible traces or residue may be left behind. The duration can be in a range from about a month to a few years. However, the duration is typically in a range from about one month to twelve months, or in some embodiments, six to twelve months. It is important for the stent to provide mechanical support to a vessel for at least a portion of the duration. Many bioabsorbable polymers have erosion rates that make them suitable for treatments that require the presence of a device in a vessel for the above-mentioned time-frames.

As indicated above, it is desirable to have the capability of obtaining images of polymeric stents with x-ray fluoroscopy during and after implantation. Additionally, during a treatment period, a biodegradable stent is required to provide adequate support or maintain patency of the lumen walls for given time period. Specifically, the stent should maintain sufficient mechanical properties to oppose the inward radial force imposed by the lumen walls, including the cyclic loading induced by the beating heart. The patency should maintain or sustain such patency in spite of the degradation or erosion of the stent body. An exemplary desired degree of patency may be greater than 50% of the deployed diameter of the stent. Thus, the stent should have sufficient strength, stiffness (modulus), and creep resistance to keep recoil to an acceptable level during a given period. Therefore, an erodible stent structure should have the appropriate combination of mechanical properties and degradation or erosion properties to allow patency during a specified treatment period.

Various embodiments of the present invention include a bioabsorbable stent having a radiopaque layer that includes sufficient radiopaque material to allow visualization of the stent with X-ray imaging for fluoroscopy. In certain embodiments, the stent includes a stent body or scaffolding having a radiopaque layer and a support layer. In some embodiments, the radiopaque layer includes a radiopaque material mixed within a bioabsorbable polymer.

In certain embodiments, the primary purpose of the radiopaque layer is to allow fluoroscopic visualization of the stent during and after implantation. Additionally, the support layer may be primarily or completely responsible for providing mechanical support and maintain patency of vessel. In these embodiments, the support layer is formed from a bioabsorbable polymer. The polymer of the radiopaque layer can be the same or different from the polymer of the support layer. In other embodiments, the radiopaque layer can assist the support layer in maintaining patency.

The radiopaque layer can degrade or absorb when it comes into contact with bodily fluids during delivery and after deployment of a stent at an implant site. The radiopaque layer can be configured to be visible a sufficient amount of time for delivery and implanting the stent.

Thus, in some embodiments, the functions of visualization and support are partially or completely delegated to separate layers of the stent body. Therefore, in such embodiments, the properties of the radiopaque layer can be selected based primarily or completely on such factors as degradation rate and degree of radiopacity of the layer. The properties include the type of bioabsorbable polymer, type of radiopaque material, and concentration of radiopaque material. In particular, the concentration of the radiopaque material in the polymer can be selected to allow visualization of the stent with fluoroscopy.

At high enough concentration of some radiopaque materials, the mechanical properties of the polymer may be adversely affected. However, since the radiopaque layer is not required to provide support, in some embodiments, the concentration of the radiopaque material can be increased with or without regard to this function. Additionally, the polymer of the radiopaque layer can be selected so that the radiopaque layer erodes away during a specified time frame.

Furthermore, since the polymers in the radiopaque and support layers are both bioabsorbable, the stent can be designed to be completely degradable or absorbable. In some embodiments, such a stent can erode away substantially or completely from an implant site. In certain embodiments, the radiopaque material can be absorbable, erodible, or soluble. Additionally, the radiopaque material can be biostable, but can be carried away upon erosion of the radiopaque layer with no adverse physiological effects on a patient. Such biostable radiopaque material that is not bioabsorbable can be carried away by bodily fluids and eliminated from the body.

In certain embodiments, the support layer has a higher strength, higher modulus, higher toughness or combinations thereof than the radiopaque layer. In such embodiments, the polymer of the support layer can have a higher strength, modulus, toughness, or combinations thereof than the polymer of the radiopaque layer. In some embodiments, the support layer is formed from a polymer having strength and stiffness sufficient to maintain patency to a desired degree and sufficient toughness to resist failure or fracture of the stent body during use. The bending regions of a typical stent structure are the most susceptible to failure during use.

Alternatively, a polymer of the radiopaque layer can be selected on the basis of degradation rate, rather than the above-mentioned mechanical properties. In an exemplary embodiments, the support layer or the radiopaque layer can be formed from poly(L-lactide) (PLLA), poly(L-lactide-co-glycolide) (PLGA), poly(DL-lactide) (PDLA), polycaprolactone (PCL), poly(trimethylene carbonate) (PTMC), and polydioxanone (PDO). In other exemplary embodiments, the radiopaque layer can be formed from block, random, or alternating copolymers of two or more of the above-mentioned polymers. Exemplary copolymers include block copolymers such as PLLA-b-PCL, PLLA-co-PCL, PLLA-b-PTMC, and PLLA-co-PTMC. In exemplary embodiments, the support layer is formed form PLLA or PLGA.

Various structural embodiments of a stent body with a radiopaque layer are contemplated and are described and illustrated herein. In exemplary embodiments, the radiopaque layer is a luminal or an abluminal layer. In such embodiments, the support layer can be an abluminal layer or a luminal layer, respectively.

Figure 2A:
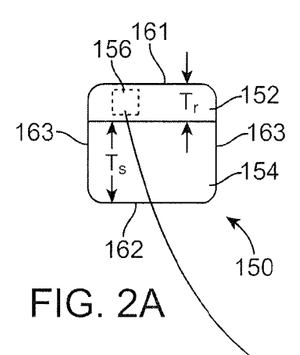
FIG. 2A depicts a cross-section of a strut with a radiopaque layer.
Figure 2B:
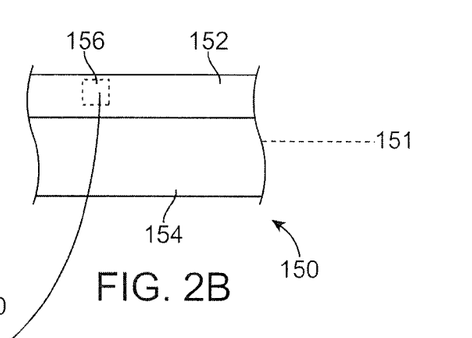
FIG. 2B depicts an axial cross section of the strut from FIG. 2A.
Figure 2C:
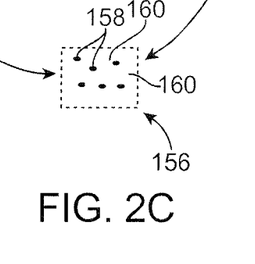
FIG. 2C depicts an expanded portion of the radiopaque layer of FIGS. 2A-B.

FIGS. 2A-C illustrate an exemplary embodiment of a strut or structural element 150 of a stent scaffolding with a radiopaque layer. FIG. 2A depicts a cross-section orthogonal to a longitudinal axis 150 of structural element 150 with an abluminal surface 161, a luminal surface 162, and sidewall surfaces 163. FIG. 2B depicts an axial cross-section of structural element 150. Structural element 150 has a radiopaque layer 152 disposed over and in contact with a support layer 154. As shown, radiopaque layer 152 is an abluminal layer, however, in alternative embodiments, radiopaque layer 152 can be a luminal layer.

As discussed above, radiopaque layer 152 includes radiopaque material mixed within a bioabsorbable polymer. The radiopaque material can be in particulate or granular form. FIG. 2C depicts an expanded portion 156 of radiopaque layer 152. As shown by FIG. 2C, radiopaque layer 152 includes particles 158 mixed within a polymer 160. Exemplary radiopaque materials can include, but are not limited to, contrast agents, biostable and erodible metals, metallic oxides, and biocompatible metallic salts. Contrast agents that are both soluble and insoluble in bodily fluids may be used.

The radiopaque layer can have a sufficient amount of radiopaque material to make the stent fluoroscopically visible. The amount of radiopaque material can be adjusted to obtain a desired degree of radiopacity. In one embodiment, the radiopaque material may be less than 5%, 5-10%, 10-20%, 20-30%, 30-40%, or greater than 40% by volume of the radiopaque layer.

As shown in FIGS. 2A-B, radiopaque layer 152 has a radial thickness Tr and support layer 154 has a radial thickness (Ts). In some embodiments, the radial thickness of the radiopaque layer can be adjusted to provide a desired degree of fluoroscopic visibility. Additionally, the thickness of the support layer can be adjusted so that the stent maintains a desired degree of patency of a lumen, such as, less than 50%, 50-60%, 60-80%, 80-95%, or greater than 95% of the deployed diameter of the stent. In exemplary embodiments, the thickness of a radiopaque layer can be less than 2 µm, 2-5 µm, 5-15 µm, 15-20 µm, 20-50 µm, 50-80 µm, 80-100 µm, or greater than 100 µm. Also, in exemplary embodiments, the support layer is less than 2, 2-5, 5-10, or more than 10 times thicker than the radiopaque layer.

As indicated above, a stent body or scaffolding can be formed by cutting a stent pattern into a tube. In certain embodiments, a stent of the present invention can be fabricated from a tube having more than one layer of which at least one is a radiopaque layer and at least one is a support layer. As described in more detail below, such a tube can be formed by coextrusion. In such embodiments, a stent pattern is cut into the layered tube to form a stent scaffolding. The stent scaffolding can include a scaffolding support layer formed from the tube support layer and a scaffolding radiopaque layer formed from the tube radiopaque layer.

Figure 3A:
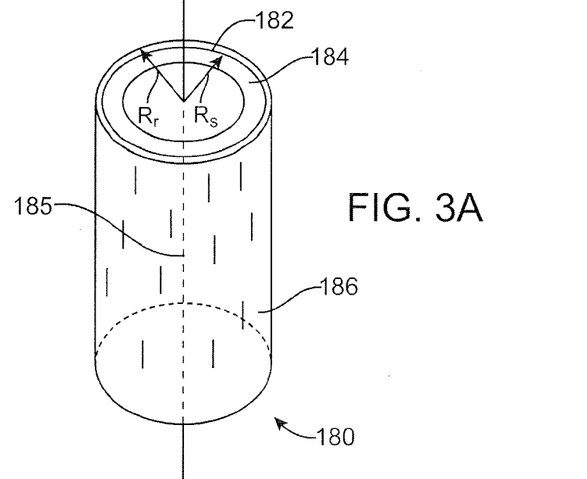
FIG. 3A depicts a perspective view of a tube with an inner layer and an outer layer.
Figure 3B:
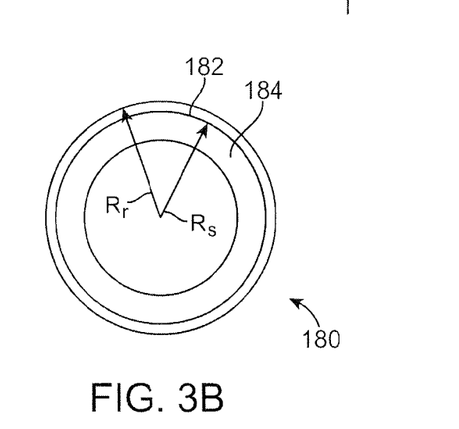
FIG. 3B depicts a radial cross-section of the tube of FIG. 3A.
Figure 3C:
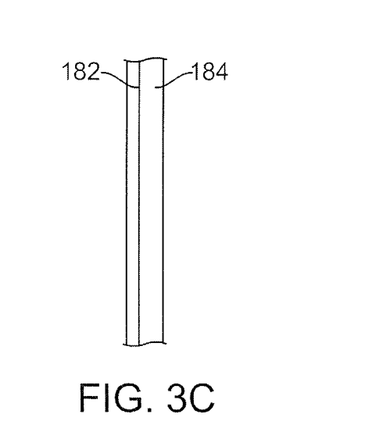
FIG. 3C depicts a cross-section of the wall of a tube parallel to the axis of the tube of FIGS. 3A-B.

FIG. 3A depicts a perspective view of a tube 180 with an outer surface 186 and cylindrical axis 185. The wall of tube 180 has two concentric or substantially concentric layers, an outer layer 182 and an inner layer 184. Outer layer 182 which has an outer radius, Rr, is a radiopaque layer including radiopaque material mixed within a bioabsorbable polymer. Inner layer 184, which has an outer radius Rs is formed from a bioabsorbable polymer and with a thickness suitable for a support layer of a stent scaffolding. FIG. 3B depicts a radial cross-section of tube 180 and FIG. 3C depicts a cross-section of the wall of tube 180 parallel to axis 185 of tube 180.

Figure 4:
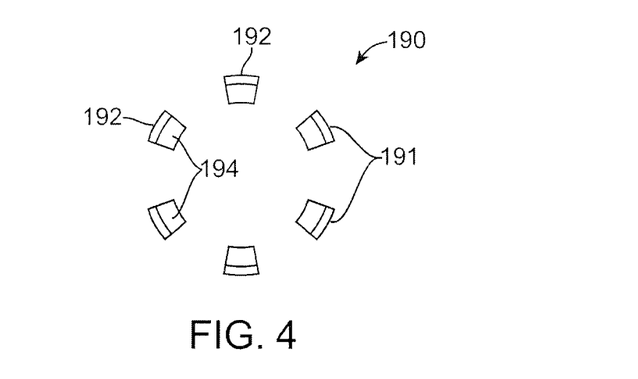
FIG. 4 depicts a radial cross-section of a stent scaffolding cut from the tube of FIGS. 3A-C.

FIG. 4 depicts a radial cross-section of a stent scaffolding 190 cut from tube 180. Stent scaffolding 190 has structural elements 191 which have an abluminal radiopaque layer 192 and a luminal support layer 194. Radiopaque layer 192 is formed from outer layer 182 of tube 180 and support layer 194 is formed from inner layer 184 of tube 180. In further embodiments, a stent scaffolding having more than two layers can be formed from a tube having more than two radial layers.

In certain embodiments, a tube with more than one layer with at least one radiopaque layer can be formed by co-extrusion. In such embodiments, a tube can be co-extruded to have a radiopaque layer and a support layer, the radiopaque layer having a radiopaque material mixed within a bioabsorbable polymer and the support layer formed from the same or different bioabsorbable polymer.

In general, extrusion refers to the process of conveying a polymer melt through an extruder and forcing the polymer melt through a die that imparts a selected shape to the polymer exiting the extruder. In the case of tubing extrusion, the polymer melt (extrudate) forced through the die forms a cylindrical film in the shape of a tube. The film is cooled and drawn axially to form the final tube product.

An extruder generally includes a barrel through which a polymer melt is conveyed from an entrance to an exit port. The polymer can be fed to the extruder barrel as a melt or in a solid form below its melting temperature. The solid polymer is melted as it is conveyed through the barrel. The polymer in the extruder barrel is heated to temperatures above the melting temperature (Tm) of the polymer and exposed to pressures above ambient. The polymer within the barrel is mixed, for example, through the use of rotating screws. Representative examples of extruders for use with the present invention may include single screw extruders, intermeshing co-rotating and counter-rotating twin-screw extruders and other multiple screw masticating extruders.

In certain embodiments, the extrudate for forming a radiopaque layer can include a polymer melt and radiopaque material in the form of particles. In some embodiments, the polymer/radiopaque material mixture can be formed first and then fed to an extruder for forming the layered tubing. In other embodiments, the polymer and radiopaque polymer can be fed separately to the extruder and mixed or compounded within the extruder.

The polymer melt exits the extruder to a die placed at the end of the extruder barrel. A die generally refers to a device having an orifice with a specific shape or design geometry that it imparts to a polymer melt pumped from an extruder. In the case of tubing extrusion, the die has a circular shaped orifice that imparts a cylindrical shape to the polymer melt exiting the die. The function of the die is to control the shape of the polymer melt by delivering polymer melt to the orifice. The polymer melt can be delivered at a constant rate, temperature, and pressure.

Co-extrusion refers to the process of extruding two or more materials through a single die with two or more orifices arranged so that the extrudates from the separate orifices merge and weld together into a laminar structure before cooling or chilling. Each material can be fed to the die from a separate extruder, but the orifices may be arranged so that each extruder supplies two or more layers of the same material. In the case of tubing co-extrusion, the die can include concentric circular slits through which the different materials exit to form a tube with two or more layers.

Figure 5:
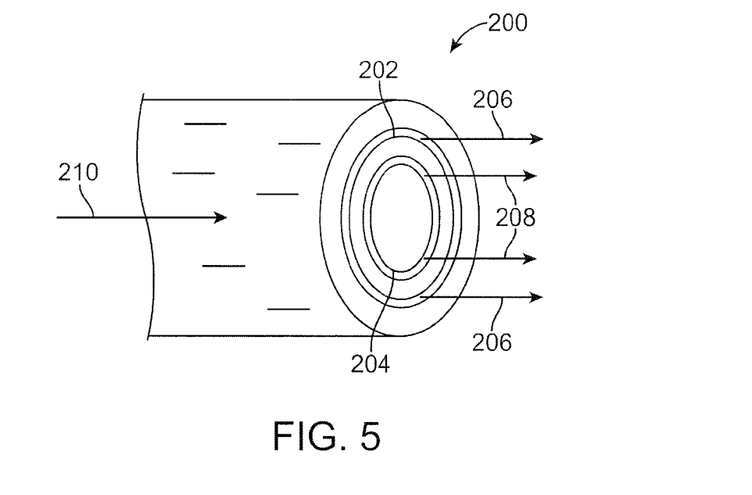
FIG. 5 depicts an extrusion die having two circular orifices, an outer orifice and an inner orifice.

In some embodiments of the present invention, an extrudate including polymer and radiopaque material is formed in one extruder and fed to a die with two or more circular orifices for formation of the layered tube. In an exemplary embodiment, FIG. 5 depicts a die 200 having two circular orifices, an outer orifice 202 and an inner orifice 204. An extrudate including a polymer/radiopaque material can exit through outer orifice 202, as shown by arrows 206, while an extrudate corresponding to a support layer can exit through inner orifice 204, as shown by arrows 208. The extrudates are conveyed through die 200, in the direction of an arrow 210. The exiting extrudates merge and are welded together form a cylindrical layered film which is cooled to form a tube.

In some embodiments, a layered tube can be radially expanded to an expanded state prior to cutting the stent pattern. The layered tube and also be axially deformed. The radial expansion increases the radial strength of the tube and a stent formed therefrom. It has also been observed that radial expansion also enhances the fracture toughness of formed stents, in particular, the resistance to the fracture and breaking of struts. In such embodiments, the tube can be radially expanded by a known method and the stent pattern can be cut into the tube in its expanded state.

In certain embodiments, a layered polymeric tube may be radially deformed by blow molding. A balloon blowing apparatus may be adapted to radially deform a polymer tube. In blow molding, a tube can be deformed radially by conveying a fluid into the tube which increases the internal pressure in the tube. The polymer tube may be also be deformed axially by applying a tensile force by a tension source at one end while holding the other end stationary. Alternatively, a tensile force may be applied at both ends of the tube. The tube may be axially extended before, during, and/or after radial expansion.

In some embodiments, blow molding may include first positioning a tube in a cylindrical member or mold. The mold controls the degree of radial deformation of the tube by limiting the deformation of the outside diameter or surface of the tube to the inside diameter of the mold. The inside diameter of the mold may correspond to a diameter less than or equal to a desired diameter of the polymer tube.

The temperature of the tube can be heated to temperatures above the Tg of the polymer during deformation. The polymer tube may also be heated prior to, during, and subsequent to the deformation. In some embodiments, the tube may be heated by translating a heating source along the cylindrical axis of the tube. As the heat source translates and heats the tube, the radial deformation propagates along the axis of the tube. In other embodiments, in addition to the heat source, the tube may be heated by the mold or the fluid conveyed into the tube to expand the tube.

The polymer tube may be sealed or blocked at a distal end. The fluid, (conventionally a gas such as air, nitrogen, oxygen, argon, etc.) may then be conveyed into a proximal end of the polymer tube to increase the pressure in the tube. The pressure of the fluid in the tube may radially expand the tube. Cooling the tube helps insure that the tube maintains the proper shape, size, and length following its formation. Upon cooling, the deformed tube retains the length and shape imposed by an inner surface of the mold.

In other embodiments, a layered tube including a radiopaque layer can be fabricated by forming a coating over a surface of a tube. The coating can be formed over the inner surface, outer surface, or both. The coating can include radiopaque material mixed with a bioabsorbable polymer. The tube can be formed from a bioabsorbable polymer and with a thickness suitable for a support layer of a stent scaffolding. A stent pattern can then be cut into the coated tube to form a stent scaffolding with a radiopaque layer and a support layer.

In such embodiments, a coating material may be applied to the tube by methods known in the art such as by spraying or dipping. The coating material can be a solution including a polymer dissolved in a solvent. The solution can further include radiopaque particles suspended or dissolved in the solvent. In some embodiments, the polymer solution can also include a drug dispersed in the solution to allow the radiopaque layer to serve as a therapeutic layer. The coating material may be applied to the stent by immersing the stent in the coating material, by spraying the material onto the stent, drop coating, or by other methods known in the art. The solvent in the solution is then removed, for example, by evaporation, leaving on the stent surfaces a polymer coating with radiopaque material and in some embodiments, a drug.

Further embodiments of the stent of the present invention can include two or more radiopaque layers. Additional embodiments of the stent can also include two or more support layers. Embodiments of such stents can be fabricated in by methods described above. In particular, a tube having the selected number of layers can be formed through co-extrusion and a stent fabricated therefrom.

Figure 6A:
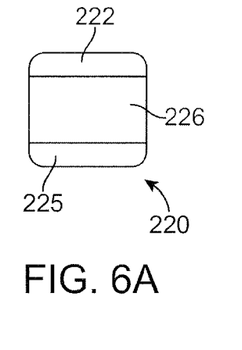
FIGS. 6A-B depicts a structural element of a stent scaffolding with an abluminal radiopaque layer and a luminal radiopaque layer with a support layer disposed between the radiopaque layers.
Figure 6B:
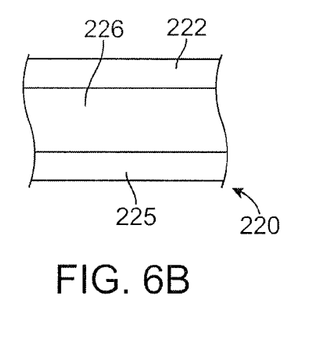

In an exemplary embodiment, the stent body includes two radiopaque layers with the support layer disposed between the two radiopaque layers. FIGS. 6A-B illustrate such an exemplary embodiment depicting a structural element 220 of a stent scaffolding with an abluminal radiopaque layer 222 and a luminal radiopaque layer 225. A support layer 226 is disposed between the radiopaque layers.

Figure 7A:
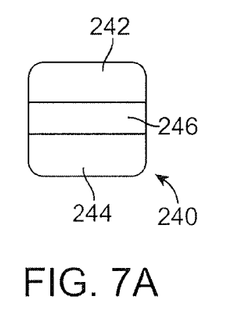
FIGS. 7A-B depict a structural element of a stent scaffolding with an abluminal support layer and a luminal support layer with a radiopaque layer disposed between the support layers.
Figure 7B:
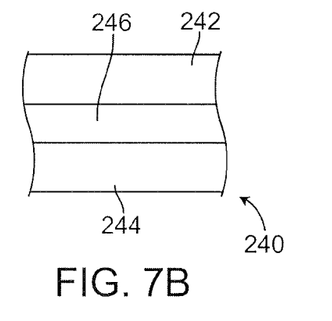

In another exemplary embodiment, the stent body includes two support layers with a radiopaque layer disposed between the two support layers. FIGS. 7A-B illustrate such an exemplary embodiment depicting a structural element 240 of a stent scaffolding with an abluminal support layer 242 and a luminal support layer 244. A radiopaque layer 246 is disposed between the support layers.

Figure 8A:
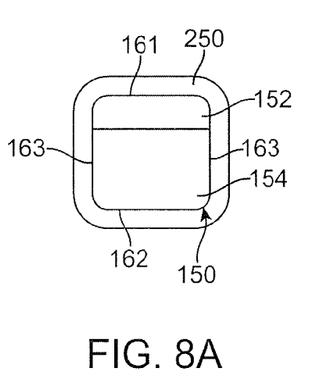
FIGS. 8A-B depicts the structural element of FIGS. 2A-B with a therapeutic layer disposed over the structural element.
Figure 8B:
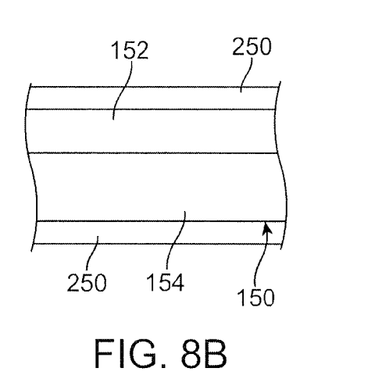

As discussed above, a medicated stent may be fabricated by coating the surface of either a metallic or polymeric scaffolding with a polymeric carrier. In further embodiments, a therapeutic agent can be incorporated within the radiopaque layer, as described above. In additional embodiments, a therapeutic layer including a drug can be formed over a stent scaffolding having a radiopaque layer. In some embodiments, the therapeutic layer can be formed above the radiopaque layer and the support layer, including the sidewalls of the stent scaffolding. FIGS. 8A-B depict the structural element of FIGS. 2A-B with a therapeutic layer 250 disposed over radiopaque layer 152 and support layer 154, including sidewalls 163. Therapeutic layer 250 is disposed over abluminal surface 161, luminal surface 162, and sidewalls 163.

Figure 9A:
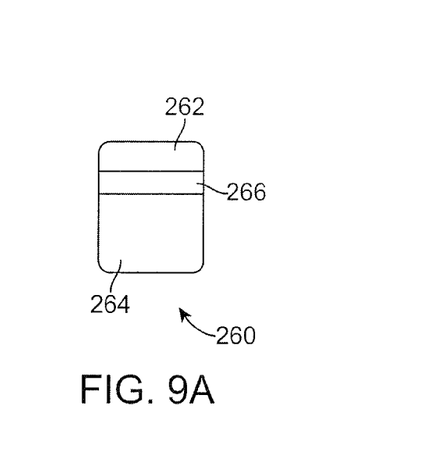
FIGS. 9A-B depicts a structural element with a radiopaque layer and a support layer with a therapeutic layer disposed therebetween.
Figure 9B:
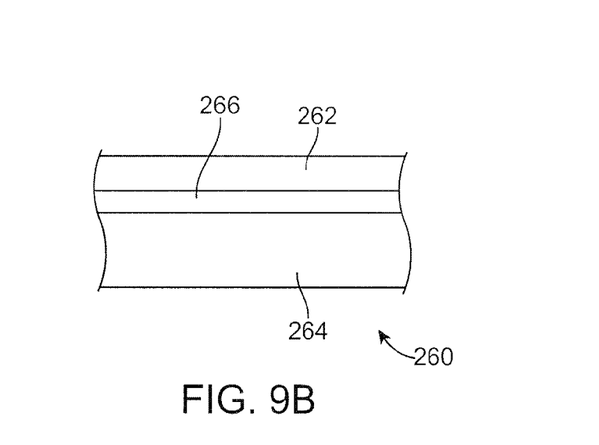

In another embodiment, a therapeutic layer can be formed between the support layer and the radiopaque layer. FIGS. 9A-B depict a structural element 260 with a radiopaque layer 262 and a support layer 264 with a therapeutic layer 266 disposed therebetween. Such a stent scaffolding can be formed by first forming a therapeutic layer over a polymer tube and then a radiopaque layer over the therapeutic layer. Then, a stent pattern in formed in the tube to form the stent scaffolding.

Representative iodinated contrast agents may include, but are not limited to, acetriozate, diatriozate, iodimide, ioglicate, iothalamate, ioxithalamate, selectan, uroselectan, diodone, metrizoate, metrizamide, iohexol, ioxaglate, iodixanol, lipidial, ethiodol, and combinations thereof. Contrast agents also include biocompatible metallic salts such as barium sulfate.

As the stent is delivered and implanted, the radiopaque layer degrades and erodes. The radiopaque layer can erode away in less than 10 minutes, 10-60 minutes, 1-2 hours, 2-10 hours, 10-24 hours, 1-7 days, 1-2 weeks, 2 weeks to a month, 1-2 months, or greater than 2 months. As the radiopaque layer erodes, radiopaque material is lost from the layer, decreasing the radiopacity and fluoroscopic visibility of the stent. The radiopaque layer can be fluoroscopically visible for less than 10 minutes, 10-60 minutes, 1-2 hours, 2-10 hours, 10-24 hours, 1-7 days, 1-2 weeks, 2 weeks to a month, 1-3 months, 3-6 months, 6-12 months, or greater than 12 months. In some embodiments, the radiopaque layer includes a sufficient amount of radiopaque material to allow the stent to be visible for a selected period of time after implantation. Although the implantation procedure may take only a few minutes, it can be advantageous to have the ability to locate the stent for a longer period of time after implantation. For example, problems may arise that may require the need to reintervene.

The bioabsorbable polymer of the radiopaque layer can be the same or different from the bioabsorbable polymer of the support layer. The required degradation time of a stent body and the time for visualization of a stent are generally different, with the former typically being longer than the latter. Thus, in some embodiments, the bioabsorbable polymer in the radiopaque layer can have a faster absorption rate than the bioabsorbable polymer body.

Generally, the life-time of the radiopaque layer can be controlled through selection of the bioabsorbable polymer in the radiopaque layer. In particular, the rate at which a layer absorbs can be tuned based on the selected time period, such as a time necessary to deliver a stent to an implant site or a longer period, such as the time needed for reintervention. The content of faster eroding polymer in the copolymer can be modified to obtain a desired absorption rate. In exemplary embodiment, the support layer can be PLLA (degradation time between 2-3 years) and the radiopaque layer can be formed from PDLA (degradation time 12-18 months), PGA (degradation time 6-12 months), or PDO (degradation time of 6-12 months). Degradation time is the time for complete absorption or erosion of a polymer construct.

In additional embodiments, the bioabsorbable polymer of the radiopaque layer can be a water soluble polymer. Exemplary water soluble polymers include poly(vinyl alcohol) (PVA) and poly(ethylene glycol) (PEG). Water soluble polymers tend to absorb faster than a non-water soluble hydrolytically degradable polymer. Thus, for a radiopaque layer of similar thickness, the radiopaque layer with a water soluble polymer can have a shorter life-time than a radiopaque layer with a non-water soluble hydrolytically degradable polymer.

Representative examples of metals that may be used as radiopaque agents include, but are not limited to, iron, magnesium, zinc, platinum, gold, and tungsten. Additionally, oxides of such metals and other metals may be used as radiopaque agents. In one embodiment, the metal can be erodible or corridible. An erodible or corrodible metal is one that has the propensity for self-dissolution in an in vivo environment. A metal that undergoes self-dissolution in an in vivo environment corrodes when subjected to bodily fluids and breaks down. A self-dissolving metal can be selected that has little or no ill effect to a patient. Representative examples of erodible metals include, but are not limited to, magnesium, zinc, tungsten, and iron.

A biocompatible metallic salt refers to a salt that may be safely absorbed by a body. Representative biocompatible metallic salts that may used in a radiopaque layer include, but are not limited to, ferrous sulfate, ferrous gluconate, ferrous carbonate, ferrous chloride, ferrous fumarate, ferrous iodide, ferrous lactate, ferrous succinate, barium sulfate, bismuth subcarbonate, bismuth potassium tartrate, bismuth sodium iodide, bismuth sodium tartrate, bismuth sodium triglycollamate, bismuth subsalicylate, zinc acetate, zinc carbonate, zinc citrate, zinc iodate, zinc iodide, zinc lactate, zinc phosphate, zinc salicylate, zinc stearate, zinc sulfate, and combinations thereof.

In some embodiments, the size the particles of radiopaque agent in a radiopaque layer can be small enough to reduce or eliminate the risk of thrombosis due to release of such particles from the coating. Reducing the size of bioabsorbable particles decreases their absorption time. In one embodiment, a dimension of the particles can be 10-100 μm, 100-200 μm, or greater than 200 μm.

In certain embodiments, the radiopaque particles can be less than 10 μm. In particular, the particles can be nanoparticles. A "nanoparticle" refers to a particle with a dimension in the range of about 1 nm to about 100 nm. Another significant advantage of smaller particles such as nanoparticles over larger particles is that nanoparticles may disperse more uniformly in a polymeric matrix, which results in more uniform radiopacity.

Representative examples of polymers that may be used to fabricate embodiments of layers of stents and coatings on stents of the present invention include, but are not limited to, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen, and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating embodiments of implantable medical devices disclosed herein include ethylene vinyl alcohol copolymer (commonly known by the generic name EVOH or by the trade name EVAL), poly(butyl methacrylate), poly (vinylidene fluoride-co-hexafluoropropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, poly(vinyl acetate), styrene-isobutylene-styrene triblock copolymers, and polyethylene glycol.

Active agents or drugs can include anti-inflammatories, antiproliferatives, and other bioactive agents. An antiproliferative agent can be a natural proteineous agent such as a cytotoxin or a synthetic molecule. Exemplary active agents can include rapamycin, everolimus, structural derivatives and functional analogues of rapamycin, structural derivatives and functional analogues of everolimus. An anti-inflammatory drug can be a steroidal anti-inflammatory agent, a nonsteroidal anti-inflammatory agent, or a combination thereof.

The examples set forth below are for: illustrative purposes only and are in no way meant to limit the invention. The following examples are given to aid in understanding the invention, but it is to be understood that the invention is not limited to the particular materials or procedures of examples.

EXAMPLES

Example 1

1. A blend of PLLA-co-PCL (90% PLLA and 10% PCL) and tungsten nanoparticles (polymer/particle ~20:1 by volume or 1:1 by weight) is prepared using a compounder at 200° C.

2. A bi-layer tube is formed by the co-extrusion of PLLA as an inner layer and the PLLA-co-PCL/tungsten nanoparticles as the radiopaque outer layer. The thickness of the PLLA outer layer and the radiopaque layer is set to 0.05 inch and 0.02 inch, respectively. The inside diameter (ID) of the extruded tubing is set to about 0.021 inch and the outside diameter (OD) is about 0.091 inch.

3. The bi-layer tube is radially expanded. A stent pattern is cut into the expanded tubing. The total thickness of the stent struts is about 0.008 inch.

Example 2

1. A blend of PLLA and barium sulfate (100:30 by weight) is prepared using a compounder at 200° C.

2. A bi-layer tube is formed by the co-extrusion of PLLA as an inner layer and the PLLA/barium sulfate as the radiopaque outer layer. The thickness of the PLLA outer layer and the radiopaque layer is set to 0.05 inch and 0.02 inch, respectively. The inside diameter (ID) of the extruded tubing is set to about 0.021 inch and the outside diameter (OD) is about 0.091 inch.

3. The bi-layer tube is radially expanded. A stent pattern is cut into the expanded tubing. The total thickness of the stent struts is about 0.008 inch.

Example 3

1. A blend of PLGA and barium sulfate (100:30 by weight) is prepared using a compounder at 200° C.

2. A bi-layer tube is formed by the co-extrusion of PLGA as an inner layer and the PLGA/barium sulfate as the radiopaque outer layer. The thickness of the PLGA outer layer and the radiopaque layer is set to 0.05 inch and 0.02 inch, respectively. The inside diameter (ID) of the extruded tubing is set to about 0.021 inch and the outside diameter (OD) is about 0.091 inch.

3. The bi-layer tube is radially expanded. A stent pattern is cut into the expanded tubing. The total thickness of the stent struts is about 0.008 inch.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of fabricating a stent comprising:
co-extruding a tube consisting of at least one radiopaque layer and at least one support layer, each radiopaque layer consisting of a radiopaque material mixed within a bioabsorbable polymer and each support layer consisting of the same bioabsorbable polymer as the radiopaque layer, wherein the radiopaque material comprises a corrodible metal, a biostable metal, metallic salts, or a combination thereof; and
cutting a stent pattern in the tube to form a stent comprising a scaffolding, the stent scaffolding consisting of a support layer and a radiopaque layer, the scaffolding support layer formed from the at least one tube support layer and the scaffolding radiopaque layer formed from the at least one tube radiopaque layer,
wherein the bioabsorbable polymer allows the radiopaque layer to erode away in greater than 2 months upon delivery and implantation of the stent.

2. The method of claim 1, wherein the co-extrusion of the tube comprises co-extrusion of a melt of the bioabsorbable polymer with a melt of the bioabsorbable polymer including the radiopaque material mixed therein.

3. The method of claim 1, wherein the stent pattern is cut by laser machining.

4. The method of claim 1, wherein the radiopaque material comprises particles.

5. The method of claim 1, wherein the support layer is adapted to be primarily responsible for maintaining patency within a vascular lumen.

6. The method of claim 4, wherein the particles have a dimension of 10-100 μm or 100-200 μm.

7. The method of claim 1, wherein the radiopaque material is platinum or gold.

8. The method of claim 1, wherein the bioabsorbable polymer is poly(L-lactide).

9. The method of claim 1, wherein the bioabsorbable polymer is poly(L-lactide-co-glycolide).

10. The method claim 1, wherein the radiopaque material is 10 to 20%, 20 to 30%, or 30 to 40% by volume of the radiopaque layer.

11. The method claim 1, wherein a thickness of the radiopaque layer is 5 to 15 microns.

* * * * *